(12) United States Patent  
Belov

(10) Patent No.: US 9,269,548 B2  
(45) Date of Patent: Feb. 23, 2016

(54) METHOD AND APPARATUS FOR COUPLING FAST SEPARATIONS AND SLOW DETECTION SYSTEMS

(75) Inventor: Mikhail E. Belov, Richland, WA (US)

(73) Assignee: BATTELLE MEMORIAL INSTITUTE, Richland, WA (US)

( * ) Notice: Subject to any disclaimer, the term of this patent is extended or adjusted under 35 U.S.C. 154(b) by 0 days.

(21) Appl. No.: 13/086,244

(22) Filed: Apr. 13, 2011

(65) Prior Publication Data

US 2012/0261564 A1   Oct. 18, 2012

(51) Int. Cl.
*H01J 49/00* (2006.01)
*H01J 49/06* (2006.01)
*G01N 27/62* (2006.01)

(52) U.S. Cl.
CPC .......... *H01J 49/0031* (2013.01); *G01N 27/622* (2013.01); *H01J 49/061* (2013.01)

(58) Field of Classification Search
CPC ... G01N 26/622; G01N 2/6227; H01J 49/004; H01J 49/0031; H01J 49/061
USPC .................................. 250/281, 282, 286, 288
See application file for complete search history.

(56) References Cited

U.S. PATENT DOCUMENTS

| | | | | |
|---|---|---|---|---|
| 6,707,036 B2* | 3/2004 | Makarov et al. | ............... | 250/288 |
| 7,456,391 B2* | 11/2008 | Zare | ........................ | H01J 49/40 250/281 |
| 8,158,932 B2* | 4/2012 | Belford | ................ | G01N 27/624 250/281 |
| 2007/0158543 A1* | 7/2007 | Clowers | ............... | G01N 27/622 250/282 |
| 2008/0067349 A1* | 3/2008 | Moskovets | ............ | H01J 49/401 250/287 |
| 2008/0185513 A1* | 8/2008 | Belov | .................. | H01J 49/0031 250/288 |
| 2008/0265173 A1* | 10/2008 | Smith | ....................... | H01J 9/14 250/396 R |
| 2009/0101810 A1* | 4/2009 | McLean | ................. | B82Y 30/00 250/282 |
| 2009/0294644 A1* | 12/2009 | Belov | .................... | G01N 27/622 250/282 |
| 2009/0294662 A1* | 12/2009 | Belov | .................. | H01J 49/4235 250/291 |
| 2010/0059673 A1* | 3/2010 | Makarov | ............. | H01J 49/0081 250/283 |
| 2010/0108879 A1* | 5/2010 | Bateman | .............. | G01N 27/622 250/283 |
| 2011/0127417 A1* | 6/2011 | Ibrahim | ................ | H01J 49/004 250/282 |

OTHER PUBLICATIONS

Belov, M, et. al., "Initial implementation of an electrodynamic ion funnel with Fourier transform ion cyclotron resonance mass spectrometry" J. Am. Soc. Mass Spectrom., 2000, 11(1), 19-23.*

* cited by examiner

Primary Examiner — Wyatt Stoffa
(74) Attorney, Agent, or Firm — James D. Matheson

(57) ABSTRACT

An apparatus and method for analyzing a sample containing multiple analytes that combines a separation device that separates the individual analytes by virtue of some physical and/or chemical characteristic other than the mass to charge ratio (m/z) interfaced with a mass spectrometer that detects the m/z of individual analytes. Separation is performed on the shorter timescale than signal detection with the mass spectrometer. A preferred embodiment utilizes an ion mobility spectrometer interfaced with an Orbitrap mass spectrometer.

19 Claims, 12 Drawing Sheets

METHOD AND APPARATUS FOR COUPLING FAST SEPARATIONS AND SLOW DETECTION SYSTEMS

TECHNICAL FIELD

This invention relates to mass spectrometry (MS) systems. Specifically, this invention relates to the interfacing systems that perform relatively fast analyte separations with MS systems.

BACKGROUND OF THE INVENTION

The past several decades have witnessed exponential progress in the health sciences and biotechnology fields. From the mapping of the human genome to the development of proteomics, today's scientific community has gained an understanding of the processes of living organisms unimaginable to earlier generations. At the core of this progress has been the development of new instruments and new techniques that have allowed scientists to correctly analyze and identify the molecules that are central to their scientific inquiry. To continue to push their progress forward, researchers in these fields are in constant in need of new instruments and/or analytical techniques that offer more precise analysis of these molecules.

One difficulty confronting current researchers is created by the fact that molecules that have structural differences can appear similar or identical in a given analysis. For example, when analyzed in a mass spectrometer, different isoforms of the same protein present the same m/z peaks, and can thus appear identical despite their structural differences.

This problem is illustrated in top-down proteomics, which may involve direct analysis of intact proteins, access to complete protein sequences, and localization and characterization of post translational modifications (PTMs) of the intact proteins. PTMs have well-documented roles in signal transduction, regulation of cellular processes, clinical biomarkers, and therapeutic targets. The identification of proteins with similar or identical mass to charge ratios thus provides an excellent example of the more general problems facing scientists seeking to provide devices and techniques that allow high resolution characterization of molecules.

One exemplary system of such analysis is a so-called Orbitrap mass spectrometer (MS). Due to high mass resolution and mass accuracy at higher molecular masses, an Orbitrap MS is an attractive detection system for biochemical analysis of intact proteins. The high resolution high mass accuracy of the Orbitrap MS provides high sensitivity detection and reliable identification of protein isoforms. However, as is the case with many MS systems, an Orbitrap MS system will not necessarily distinguish between two isoforms of the same protein. It is the different isoforms of the same protein that yield biologically significant functions, and are implicated in a variety of diseases, including Alzheimer's and cancer.

Another exemplary device used in sample analysis is a Drift Tube Ion Mobility Spectrometry (IMS). An IMS is an orthogonal to MS gas phase separation approach, which differentiate analytes by their shapes and is capable of distinguishing different protein isoforms. However, while an IMS can provide information distinguishing different protein isoforms, it does not provide high resolution and high mass accuracy of the Orbitrap MS.

The coupling of an Orbitrap system with in IMS system would appear to offer ideal separation combined with high resolution detection. However, prior to the present invention, no successful coupling of these devices has occurred, which illustrates a more general problem.

Coupling and efficient operation of a relatively fast separation system, such as an IMS, with a relatively slow MS detection system, such as an Orbitrap system, is problematic because of the different acquisition timescales. Specifically, an IMS separation proceeds relatively rapidly when compared with the analysis in the Obritrap system. Thus, while IMS instrument enables separation of different protein isoforms by their tertiary structures, a feature unavailable with current MS instrumentation, the direct injection of these analytes from the IMS to, for example, and Orbitrap MS would lose this separation data because separated ions would simply be recombined in the Orbitrap MS, due to its relatively slow acquisition time.

In contrast, in systems where a relatively slow separation is coupled with a relatively fast MS analysis, the problem does not exist because the acquisition period of the detection system is shorter than the temporal profile of a front-end separation peak, so that multiple detector measurements can be performed for any given separation peak. The fundamental issue in coupling any fast separation technique (e.g., IMS) to slower detection system (e.g., the Orbitrap or FTICR MS) is the inability to acquire a separation spectrum, as the separation completes before acquisition of a single mass spectrum.

Thus, there is a need for the effective integration and coupling of relatively fast separation techniques with relatively slower MS analysis systems. There is a further need for the ability to analyze samples wherein both the mass spectrometry and the mobility data are preserved, such that the final output is an accurate mass spectrum that retains the high resolution data from every digitized point where each ion species is identified not only by the mass to charge ratio, but also by the separation time of the various species in the sample. The present invention meets those needs.

SUMMARY OF THE INVENTION

Generally speaking, the present invention is an apparatus and a method for analyzing samples containing multiple analytes to determine both the separation time and mass to charge ratio (m/z) for each analyte. The apparatus consists of a separation device that separates the individual analytes by virtue of some physical and/or chemical characteristic other than the mass to charge ratio (m/z) of the analytes. The separation device is interfaced with a mass spectrometer, which then measures the mass to charge ratio (m/z) of the analytes.

One distinguishing feature of the present invention when compared to other devices that couple separation devices with mass spectrometers is related to the speed of the operation of the separation device when compared to the mass spectrometer. In the present invention, unlike any other prior art device, the separation device is configured to separate the individual analytes more rapidly than the mass spectrometer is configured to determine the mass to charge ratio (m/z) of the analytes. This difference in timescales requires the unique techniques and equipment to successfully interface the separation device and the mass spectrometer in a manner that preserves both the mass spectrometer's resolution and the mobility information from the separation device. These unique techniques and equipment form one aspect that distinguishes the present invention from prior art devices. The final output of the invention is thus an accurate mass spectrometer reading that retains not only the high resolution data from every digitized point where each ion species is identified by the mass to charge ratio in the mass spectrometer, but also highly accurate separation times of the various species as determined in the separation device.

Suitable separation devices for the present invention include, but are not limited to, a reverse phase chromatography device, a capillary electrophoresis device, an ion mobility spectrometer, a field asymmetric ion mobility spectrometer (FAIMS), and a gas chromatography device. Suitable mass spectrometers for the present invention include, but are not limited to, a three dimensional quadrupole ion trap, a Fourier transform ion cyclotron resonance mass spectrometer, and an Orbitrap mass spectrometer.

In most embodiments of the present invention, the analytes are ionized prior to their introduction into the separation device. For example, a preferred embodiment of the present invention uses an ion mobility spectrometer as the separation device. An ion-mobility spectrometer (IMS) is an analytical device used to separate and identify ionized molecules in the gas phase based on their mobility in a carrier buffer gas. To operate properly, the IMS must have the analytes ionized before they are introduced into the IMS. Continuing the example, the analytes are ionized prior to their introduction into the IMS, and they remain as ions when they leave the IMS.

In other embodiments of the present invention, the separation device will operate using some principle of separation that does not require ionization of the analytes prior to their introduction into the separation device. In these instances, the analytes are not ionized when they enter the separation device. However, in these embodiments, the samples are ionized when they leave the separation device, to prepare the samples for introduction into the mass spectrometer.

Those having ordinary skill in the art and the benefit of this disclosure will recognize that there are many techniques and devices that may be employed to ionize samples. The present invention may utilize any of those techniques and devices. Depending on the particular embodiment, these techniques and devices may be used either at the entrance or at the exit of the separation device. As such, those of ordinary skill in the art having the benefit of this disclosure will recognize that these techniques and devices for ionizing samples should be employed either prior to the sample's introduction into the separation device, or upon the sample leaving the separation device, as is appropriate for the specific separation device used in any particular embodiment of the present invention. The present invention is thus compatible with, and includes, all such embodiments, as the novelty of the present invention and the principles of operation apply regardless of when and where analytes are ionized in a particular embodiment.

Accordingly, it should be understood that when referring to the step of "introducing" a sample into an embodiment of the present invention that uses a particular separation device that requires ionization prior to introduction of the sample into the device, (such as an IMS), the step of "introducing" the sample would include the ionization of the sample. In the same manner, in embodiments where a separation device is used that does not require ionization, the step of "introducing" the sample into the separation device would not include ionization of the sample.

Also, in embodiments where the separation device requires ionization, the step of "introducing" the sample into the mass spectrometer would not include the ionization of the sample, as the sample would have already been ionized prior to its introduction into the separation device. Alternatively, in embodiments of the present invention where a separation device is used that does not require ionization, the step of "introducing" the sample into the mass spectrometer would then include ionization of the sample at the end of the separation device, as the sample would not have been ionized prior to its introduction into the separation device.

Whether the samples are ionized before or after the separation device, the separation device is interfaced with an ion gate which is used to control the flow of ions into the mass spectrometer. The ion gate is controlled by a control circuitry, which is configured to cause the ion gate to alternately transmit or block the analytes exiting the separation device at the entrance of the mass spectrometer. The mass spectrometer detects the m/z of individual analytes that are transmitted into the mass spectrometer by the ion gate. Analytes that are blocked by the ion gate are discarded. It is preferred that the ion gate be a Bradbury Nielsen gate used in combination with two grids that minimize lateral field extent.

Those having skill in the art will note that different mass spectrometry methods require different steps to determine the m/z spectra. For example, in three dimensional quadrupole ion traps, ions are ejected from a device using the ramping of the amplitude of an rf field. In this manner, the m/z of any ejected ion is determined directly according to the amplitude of the instrument at the time the ion was ejected. In contrast, a three dimensional electrostatic ion trap instrument (such as the orbitrap instrument manufactured by ThermoFischer Scientific) operates by oscillating the ions in a static field. The induced charge generated by these oscillations are a function of the ion's m/z, therefore the ions oscillations are measured as an analog signal in the time domain, which is then digitized and converted to a frequency spectrum using a Fourier transform. Given a known relationship between the frequency and the m/z, this information is then converted into m/z spectra for all of the ions in a particular sample. As will be apparent to those having ordinary skill in the art, this general operating principle is also applicable to Fourier transform ion cyclotron resonance instruments.

The present invention is thus designed and intended to be compatible with all of the forgoing methods. Accordingly, the step of "determining the encoded separation and m/z spectra of the separated analytes transmitted to the mass spectrometer" is accomplished in a manner that is consistent with the specific characteristics of a particular mass spectrometer instrument, and the invention should in no way be limited by the particular characteristics of any specific mass spectrometer instrument.

The method of the present invention thus performs the steps of first providing a separation device that separates the individual analytes over a period of time by virtue of some physical and/or chemical characteristic other than the mass to charge ratio (m/z). The method then provides a mass spectrometer that determines the m/z of individual analytes at a rate that is slower than the temporal width of an analyte packet/band in the separation device. Multiple portions of the sample are then introduced into the separation device at known time intervals, and the individual analytes within each portion of the sample are then separated in the separation device, thereby producing a flow of the separated analytes out of the separation device. The flow of separated analytes exiting the separation device is then divided into a series of temporal windows. Each temporal window consists of the flow of separated analytes exiting the separation device during a period of time defined for the temporal windows. The period of time can be any period of time selected by the user, but it should be shorter than the shortest peak width of the individual analytes, so that any individual analyte will be contained within at least one, and preferably more than one, temporal window. The temporal windows are also defined by a known time interval from the introduction of at least one of the multiple portions of the sample injected into the separation device. In this manner, the ions contained in each temporal window are defined both by the duration of the temporal window, and the time interval between the time window and at least one of the multiple portions of the sample injected into the separation device.

Analytes from at least one of the series of temporal windows are then introduced into the mass spectrometer. As described above, the ions in each of the temporal windows are introduced into the mass spectrometer by having the control circuitry of the ion gate transmit the analytes exiting the separation device into the entrance of the mass spectrometer. Ions outside of the temporal windows are not introduced into the mass spectrometer and are instead blocked by the ion gate, and discarded. The mass spectrometer then acquires an m/z spectrum of all the analytes which were transmitted.

Beginning with the step of introducing multiple portions of the sample into the separation device at known time intervals, the process is then repeated at different time intervals from the introduction of at least one of the multiple portions of the sample injected into the separation device. In this manner, data representing the m/z of all of the ions found at each temporal time window is generated by the mass spectrometer. From this data, the encoded separation and m/z spectra of the separated analytes transmitted to the mass spectrometer is determined. Finally, the encoded separation and m/z spectra of the separated analytes is decoded using an inverse matrix transform, revealing both the high resolution data from every digitized point where each ion species was identified by the mass to charge ratio in the mass spectrometer, and highly accurate separation times of the various species as determined in the separation device. Not to be limiting, it is preferred that the flow of separated analytes consist of analytes intermingled from two or more of the portions of the sample introduced into the separation device.

BRIEF DESCRIPTION OF THE DRAWINGS

The following detailed description of the embodiments of the invention will be more readily understood when taken in conjunction with the following drawings, wherein.

DETAILED DESCRIPTION OF THE PREFERRED EMBODIMENTS

Figure 1:
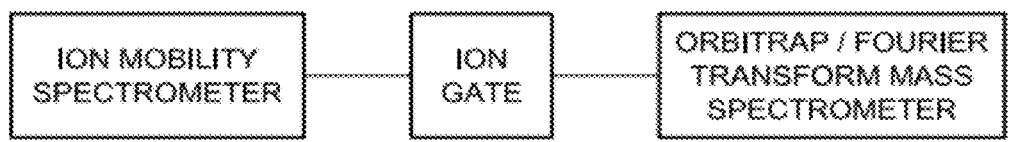
FIG. 1 is a schematic illustration of a preferred embodiment of the apparatus of the present invention coupling an ion mobility spectrometer with and ion gate and an Obritrap or Fourier Transform Mass Spectrometer.

For the purposes of promoting an understanding of the principles of the invention, reference will now be made to the embodiments illustrated in the drawings and specific language will be used to describe the same. It will nevertheless be understood that no limitations of the inventive scope is thereby intended, as the scope of this invention should be evaluated with reference to the claims appended hereto. Alterations and further modifications in the illustrated devices, and such further applications of the principles of the invention as illustrated herein are contemplated as would normally occur to one skilled in the art to which the invention relates.

An exemplary device was constructed and tested to demonstrate a preferred embodiment of the present invention. This exemplary device merely demonstrated the approach, which is broadly applicable to any combination of devices providing 'fast' separation and 'slow' detection. The terms 'fast' and 'slow' are related to the temporal profile of a peak exiting a separation device and an acquisition time of the detection system, respectively. If the temporal profile of the separation peak is shorter than the detector acquisition time, a separation dispersion spectrum becomes immeasurable with such a detector using the conventional approach of 'nested' separations.

The combination of fast separation and slow detection used to demonstrate a preferred embodiment of the present invention is an integrated system encompassing an Ion Mobility Spectrometry (IMS) separation device and an Ortibtrap Mass Spectrometer (Orbitrap MS). IMS is a gas phase separation typically performed on the time scale of several ms with a separation peak width of several hundred µs, while the Orbitrap MS provides high resolution acquisition of a mass-to-charge ratio (m/z) spectrum occurring within several hundred ms. The coupling of IMS to Orbitrap MS is accomplished with an Ion Gate, which is designed to modulate ion packets exiting the IMS instrument. FIG. 1 shows the schematic diagram of the integrated IMS-Orbitrap MS system. At known time intervals, the Ion Gate modulates the ion packets exiting IMS instrument to be either further transmitted or blocked at the entrance to the Orbitrap MS.

Figure 2:
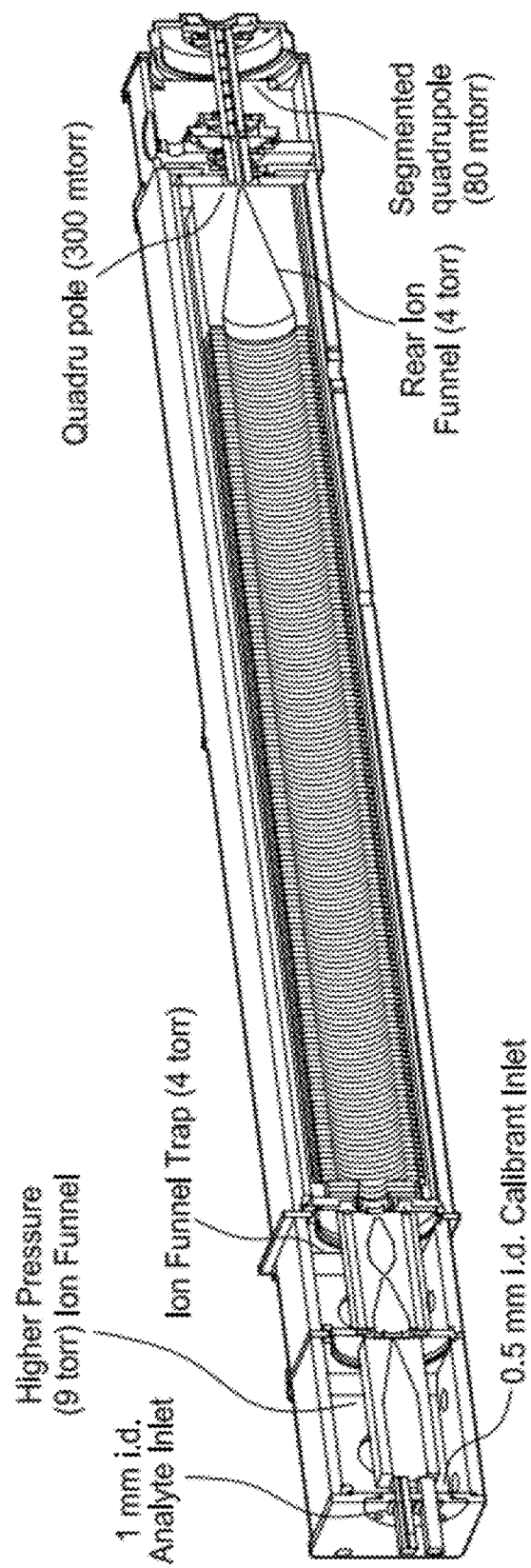
FIG. 2 is an illustration of the ion mobility spectrometer used in a preferred embodiment of the apparatus of the present invention.

FIG. 2 shows an assembly drawing of the IMS instrument. Biochemical samples are ionized with an Electrospray Ionization Source (ESI). ESI-generated droplets are introduced into the IMS instrument through a large diameter heated inlet capillary. Droplet desolvation mostly occurs in the inlet capillary and the intact molecular ions exiting the inlet are efficiently captured by an electrodynamic Ion Funnel (IF) operating at a pressure of ~10 torr. Additional desolvation of the finely dispersed droplets occurs in the IF due to radio frequency (RF) heating. Droplets are introduced into the IMS instrument off-axis to reduce gas flow into an Ion Funnel Trap (IFT) located downstream of the IF and to minimize instrument contamination. Ions exiting the IF are then trapped and accumulated in the IFT between the entrance and the trapping/exit grids. This region of the device is characterized by the constant diameter electrodes and is operated at a pressure of ~4 torr. Higher density ion packets are then introduced into a drift tube of the IMS instrument.

Figure 3:
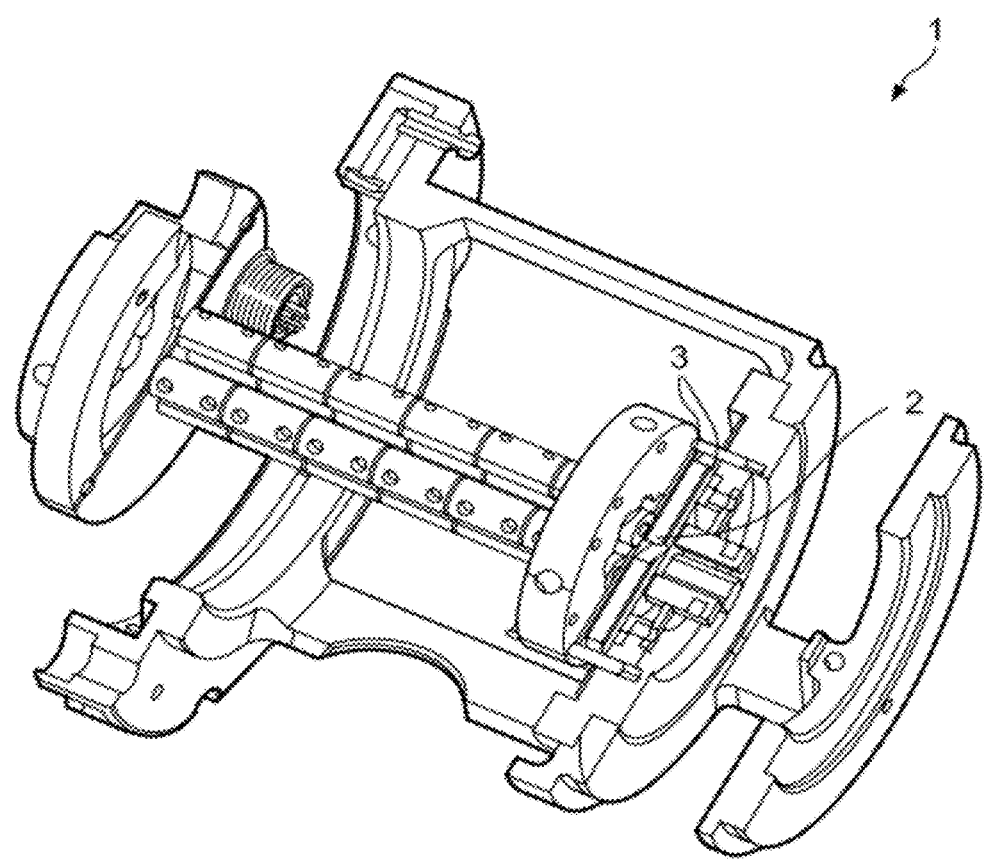
FIG. 3 is an illustration of the ion gate used in a preferred embodiment of the apparatus of the present invention.
Figure 4:
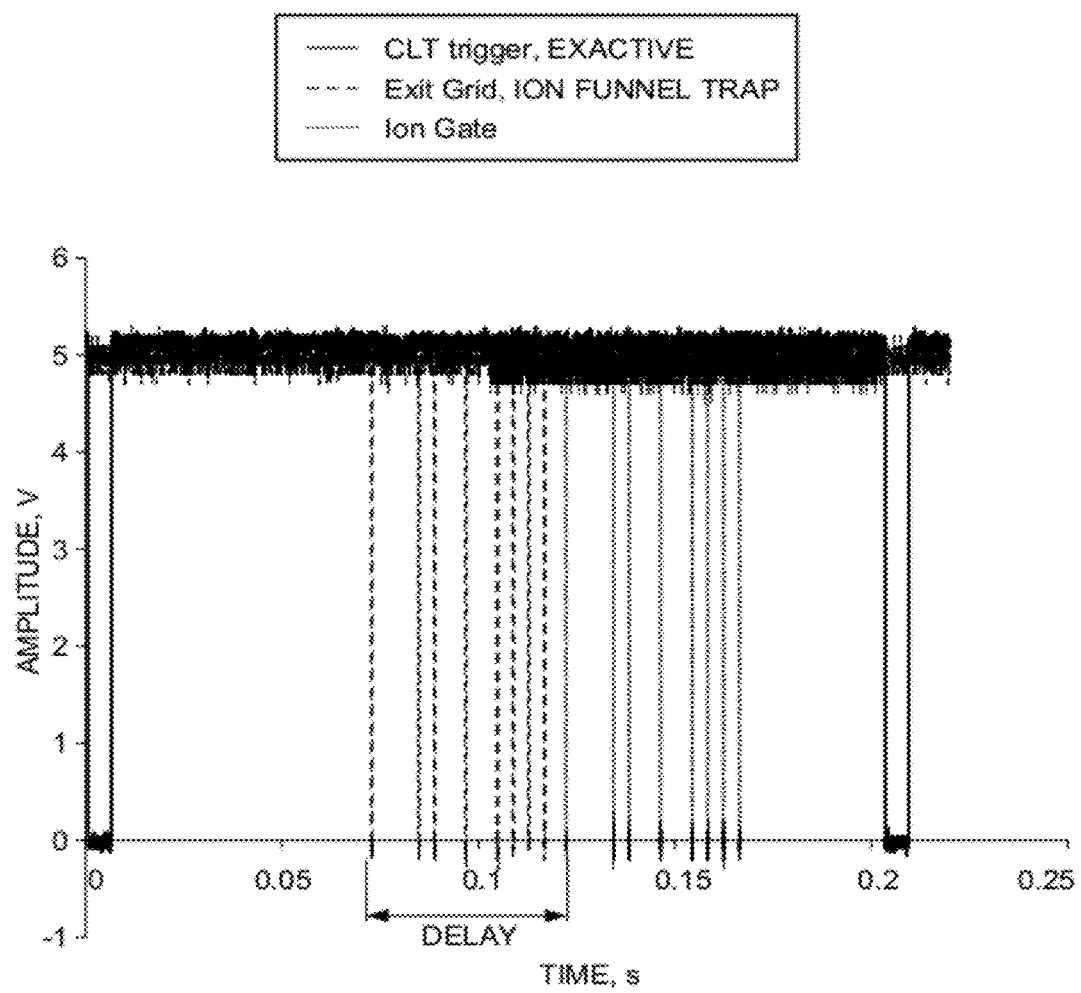
FIG. 4 is a timing diagram of the trigger pulse from the Curved Linear Trap (CLT) in the Orbitrap MS, the modulation pulses of the IFT exit grid and the Ion Gate in a preferred embodiment of the apparatus of the present invention.

Ion packet introduction is controlled by a pseudo-random binary sequence, as shown in FIG. 4, so that multiple ion packets are present in the IMS drift tube on the time scale of a single IMS separation. This approach is termed 'multiplexing'. While in the drift tube, the ion packets isotropically disperse due to diffusion and space charge repulsion, and need to be refocused into a narrow aperture of the MS interface. This is achieved with a Rear Ion Funnel (RIF) located at the IMS instrument exit. Once re-collimated with RIF, the ion packets are introduced into a differentially pumped RF quadrupole interface. As shown in FIG. 3, the Ion Gate is situated downstream of the quadrupole interface and is used to modulate ion packets at the entrance to the mass spectrometer. As shown in FIG. 3, Ion Gate 1 includes a Bradbury Neilson gate 2, and two grids 3 on either side of Bradbury Neilson gate 2.

The modulation sequence can be comprised of a single pulse or multiple pulses. These two approaches are further referred to as single and double multiplexing, respectively. FIG. 4 shows the timing diagram of the trigger pulse from Curved Linear Trap (CLT) in the Orbitrap MS, and the modulation pulses of the IFT exit grid and the Ion Gate. Low levels of the depicted waveforms correspond to ion transmission and are referred to as the Ion Gate open events, while higher levels result in the ion blocking and referred to as Ion Gate close events. In the course of multiplexed experiment (single or double), ions from multiple ion packets intermingle in the IMS drift tube, and different ion species from different injections into the drift tube arrive at the Ion Gate at the same time. These intermingled ion packets are then transmitted through the Ion Gate during the gate open events, and blocked during the gate closed events. In the single multiplexed experiment, only a single pulse is applied to the Ion Gate per IMS separation. Multiple modulation pulses applied to the Ion Gate enable double multiplexed acquisition. Once transmitted through the Ion Gate, intermingled ion packets are accumulated in the CLT of the Orbitrap MS and then transferred to the Orbitrap for further trapping and signal detection.

Figure 5:
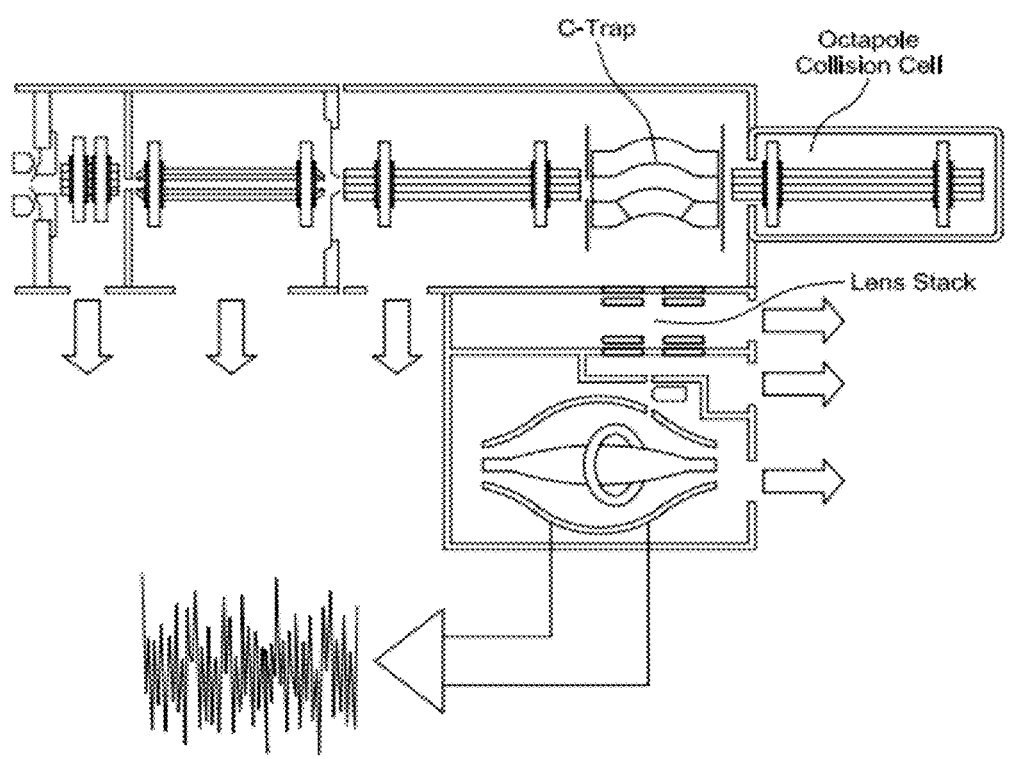
FIG. 5 is a schematic illustration of an Obritrap Mass Spectrometer used in a preferred embodiment of the apparatus of the present invention.

A schematic diagram of the Orbitrap MS is shown in FIG. 5. Per IMS separation and irrespectively of the modulation scheme (single or double), only a single m/z spectrum is acquired with the Orbitrap MS. This m/z spectrum represents an encoded snap-shot of the IMS separation domain. To acquire complete separation spectrum, the modulation sequence at the Ion Gate needs to be sequentially shifted relative to the encoding sequence at the IFT exit grid, while acquiring m/z spectra at every delay time step (see 'Delay' in FIG. 4). The result of this acquisition is the encoded 2D spectrum which contains both the IMS and m/z profiles of the species present in the biochemical sample.

Experimental results using the device described above and shown in the Figures were obtained with a polymer mixture typically used for mass spectrometer calibration.

Figure 6:
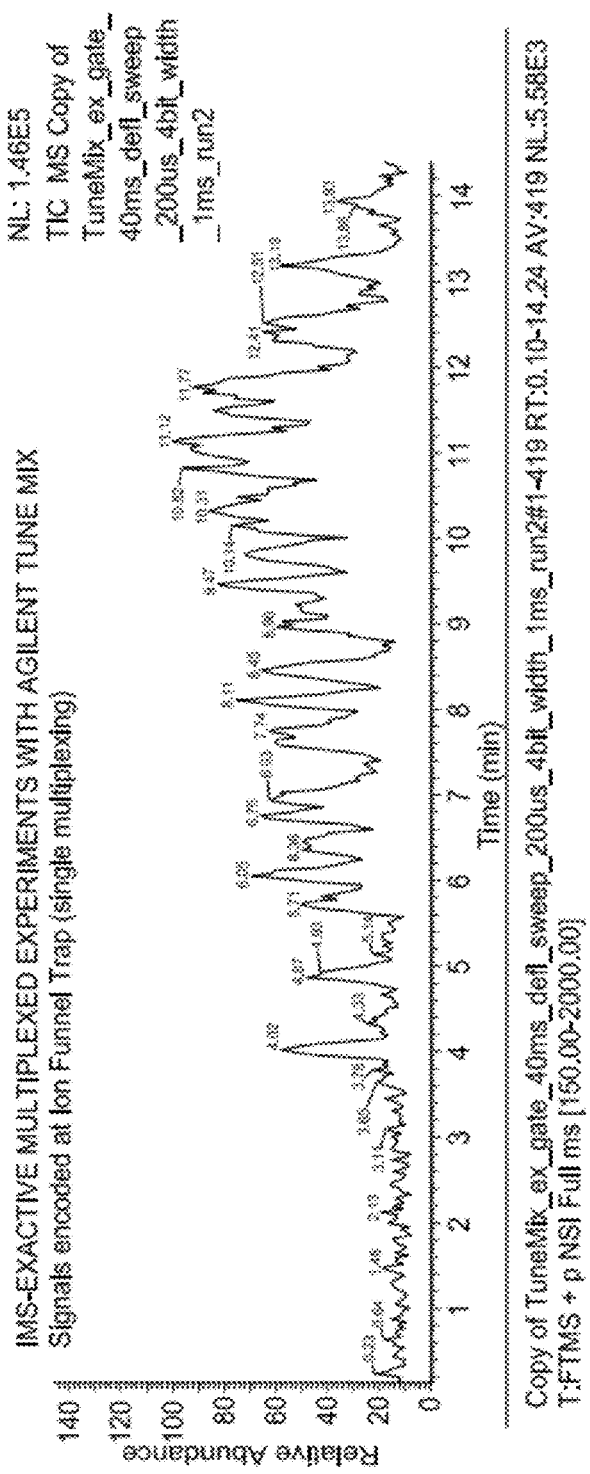
FIG. 6 is a graph showing the raw data file acquired with IMS-Orbitrap MS using single multiplexed mode in an experiment demonstrating a preferred embodiment of the apparatus of the present invention.
Figure 6:
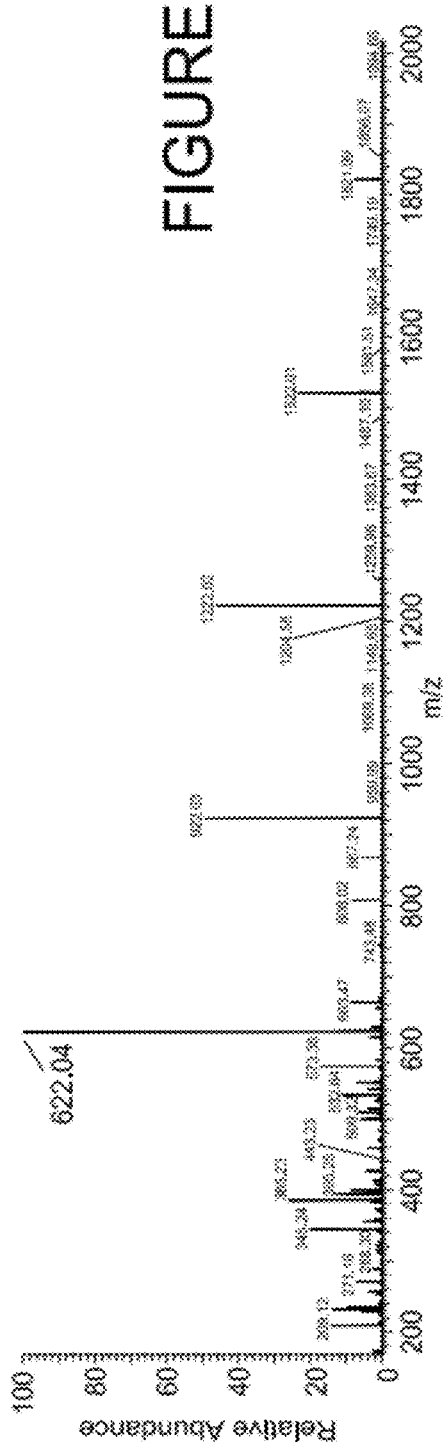

FIG. 6 shows raw data file acquired with IMS-Orbitrap MS using single multiplexed mode. In this mode, ion packet introduction into the IMS drift tube was governed by a 4-bit pseudo-random binary sequence. The Ion Gate was modulated only once per IMS separation using a 500 µs pulse. The top panel shows the encoded separation spectrum of all species present in the sample. The bottom panel depicts the summed m/z spectrum.

Figure 7:
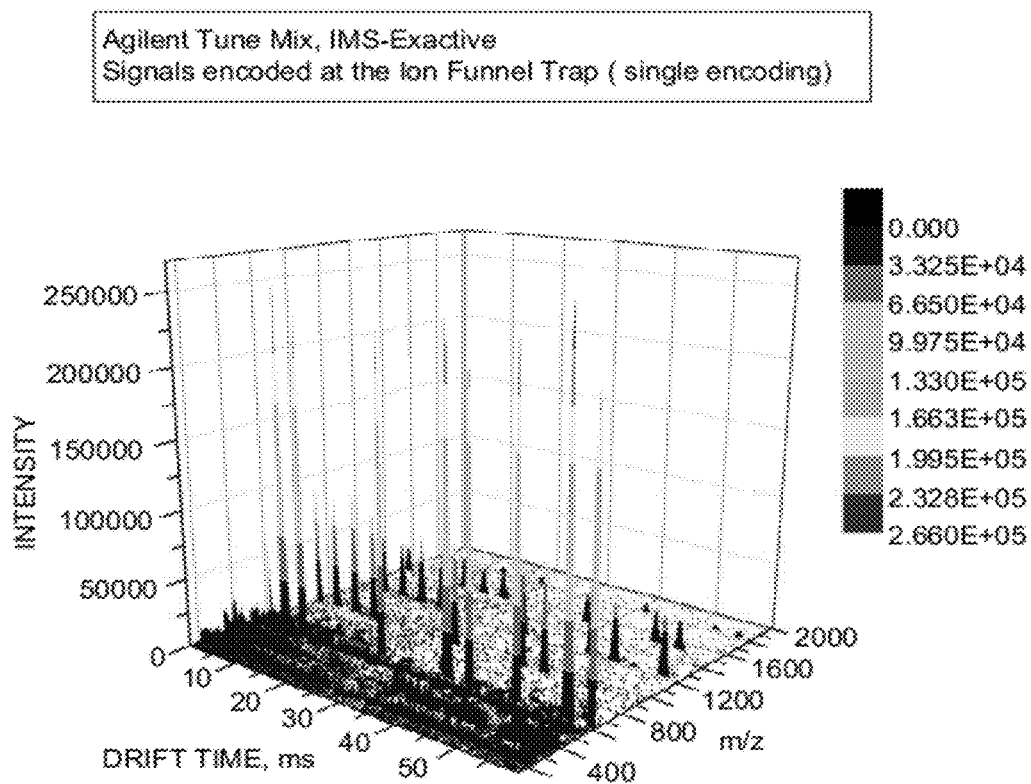
FIG. 7 is a graph showing the 3D surface plot of the data shown in FIG. 6, showing that species at a given m/z were injected multiple times into the Orbitrap MS during the signal encoding procedure in an experiment demonstrating a preferred embodiment of the apparatus of the present invention.

FIG. 7 shows the 3D surface plot of the data shown in FIG. 6 that shows that species at a given m/z were injected multiple times into the Orbitrap MS during signal encoding procedure. This plot was obtained by folding the 1D raw file in FIG. 6 by taking into account the encoding sequence. For example, the 4-bit encoding sequence has $2^N-1$ elements, equal to 15. The encoding sequence was zero filled to obtain 40-fold oversampling. This results in representation of each '1' modulation bin as 0000 . . . 01 and each '0' modulation bin as 0000 . . . 00. The 40 elements within each modulation bin are then referred to as sub-modulation bins. The total number of sub-modulation bins in such an extended sequence is 15×40=600. Given an internal clock of the IMS instrument of 100 µs, the extended sequence was equal to 60 ms, which represents IMS separation domain. During acquisition of the separation data in FIG. 6, the delay time between the first release pulse of the IFT (i.e., the first exit grid pulse) and the modulation pulse of the Ion Gate was sequentially varied by 200 µs. Therefore, the total number of steps to cover the IMS separation domain was 60 ms/200 µs=300, which is the number of spectra 1D raw file was folded to.

Figure 8:
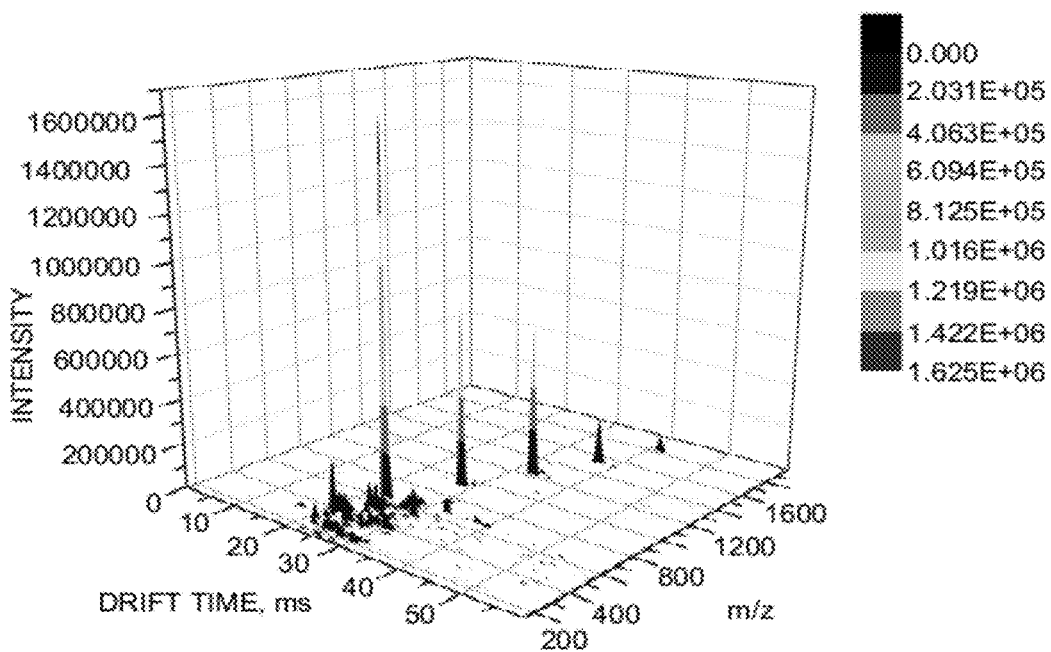
FIG. 8 is a graph showing a reconstructed 3D surface plot of the data shown in FIG. 7 in an experiment demonstrating a preferred embodiment of the apparatus of the present invention.

FIG. 8 is a 3D surface plot of the encoded data of FIG. 7. This is what would be expected in the situation where multiple isoforms of a single protein were found in a single sample. FIG. 8 shows the reconstructed 3D surface plot of the signal shown in FIG. 7. Reconstruction was performed using an inverse matrix transform. Comparison of FIGS. 7 and 8 illustrates drastic chemical background reduction and concurrent signal enhancement, as evident from the intensities of the decoded IMS-MS peaks.

Figure 9:
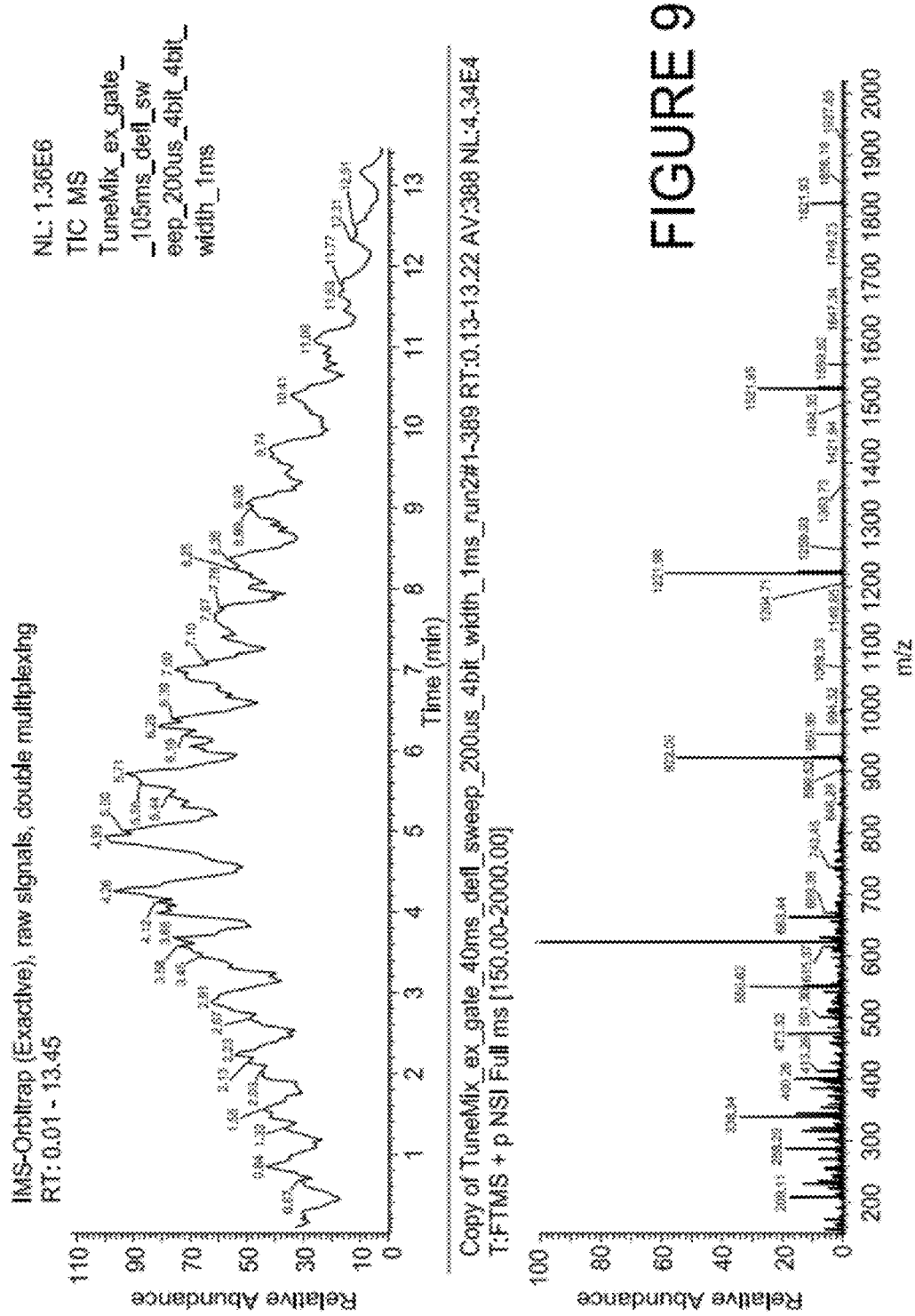
FIG. 9 is a graph showing the raw data file acquired with IMS-Orbitrap MS using double multiplexed mode in an experiment demonstrating a preferred embodiment of the apparatus of the present invention.
Figure 10:
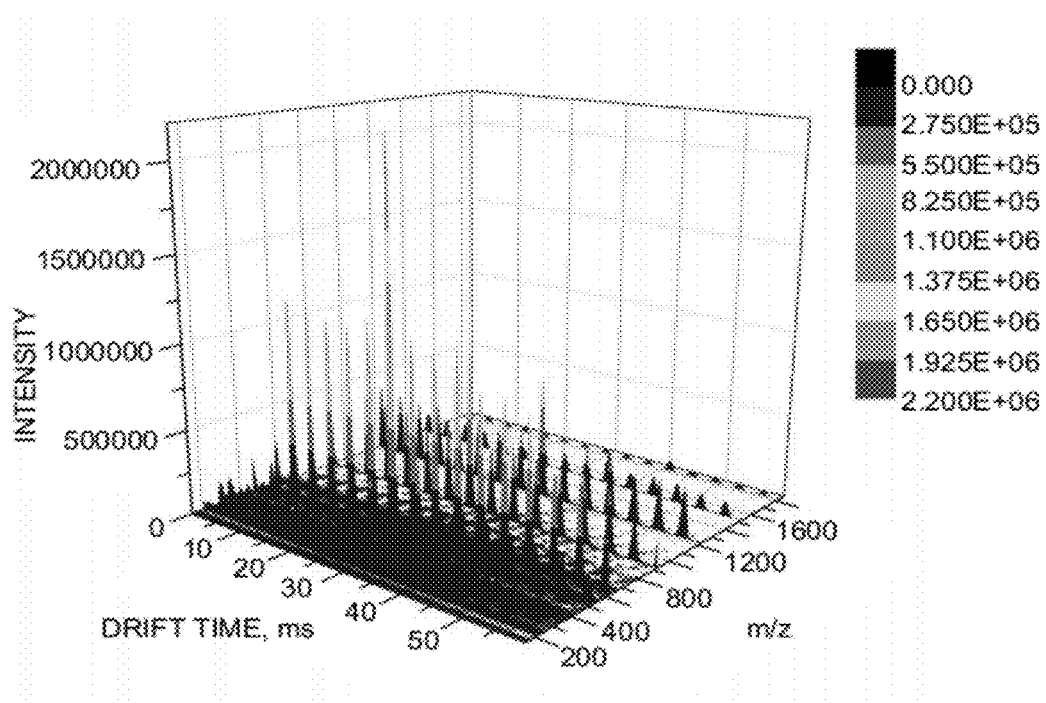
FIG. 10 is a graph showing the raw 1D separation spectrum folded into a 3D surface plot in an experiment demonstrating a preferred embodiment of the apparatus of the present invention.

FIG. 9 shows the raw data file acquired with IMS-Orbitrap MS using double multiplexed mode. Similar to the single multiplexed experiment, the ion packet introduction into the IMS drift tube was encoded with the same 4-bit pseudo-random binary sequence. Additionally, the Ion Gate was modulated with the identical 4-bit pseudo-random sequence, which results in 8-fold greater number of ions injected into the Orbitrap MS per single IMS separation as compared to the single multiplexed mode. As described above and shown in FIG. 10, the raw 1D separation spectrum was folded into the 3D surface plot.

Figure 11:
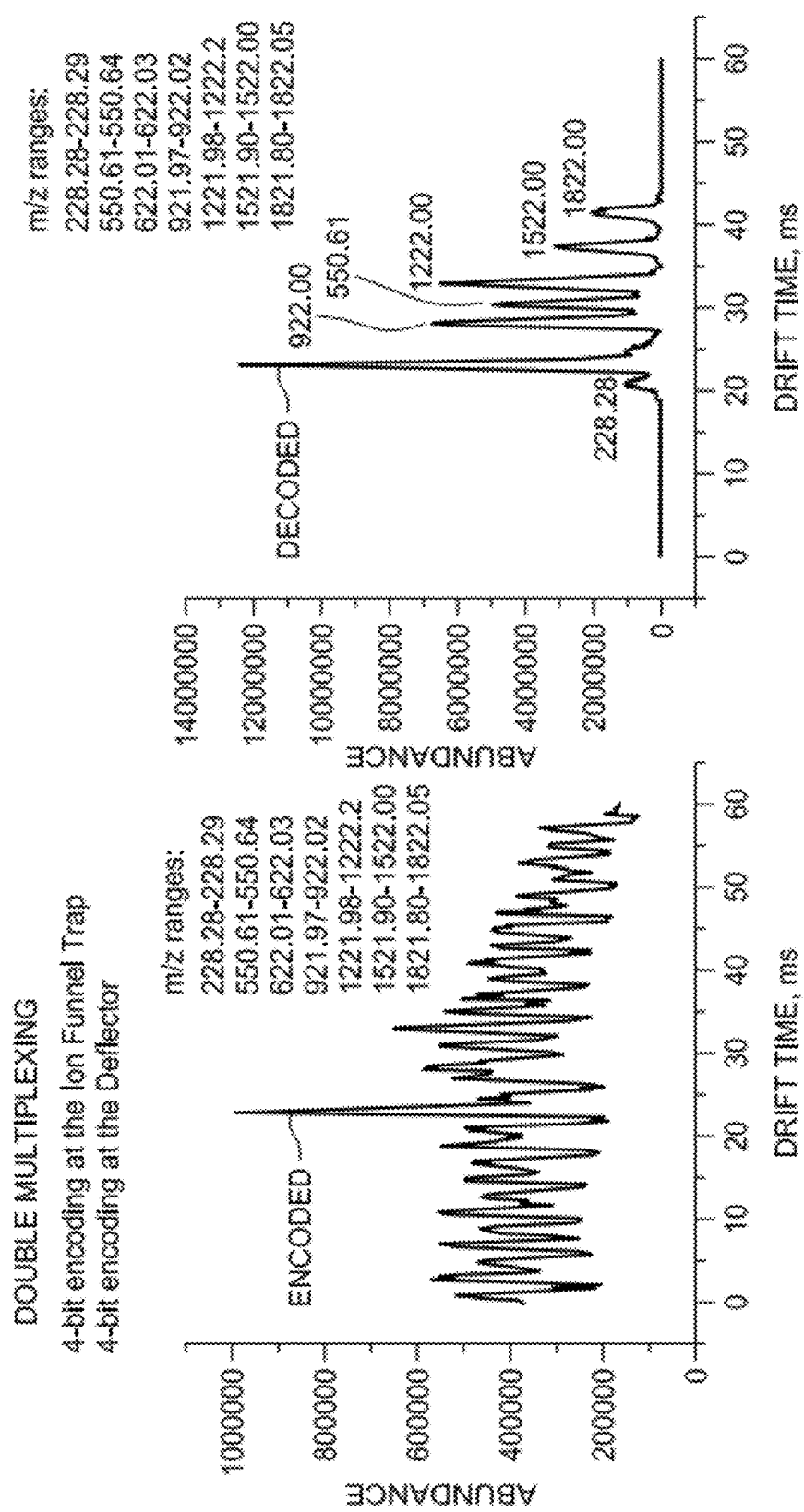
FIG. 11 is a graph showing the analysis of the double encoded and reconstructed IMS domains in an experiment demonstrating a preferred embodiment of the apparatus of the present invention.
Figure 12:
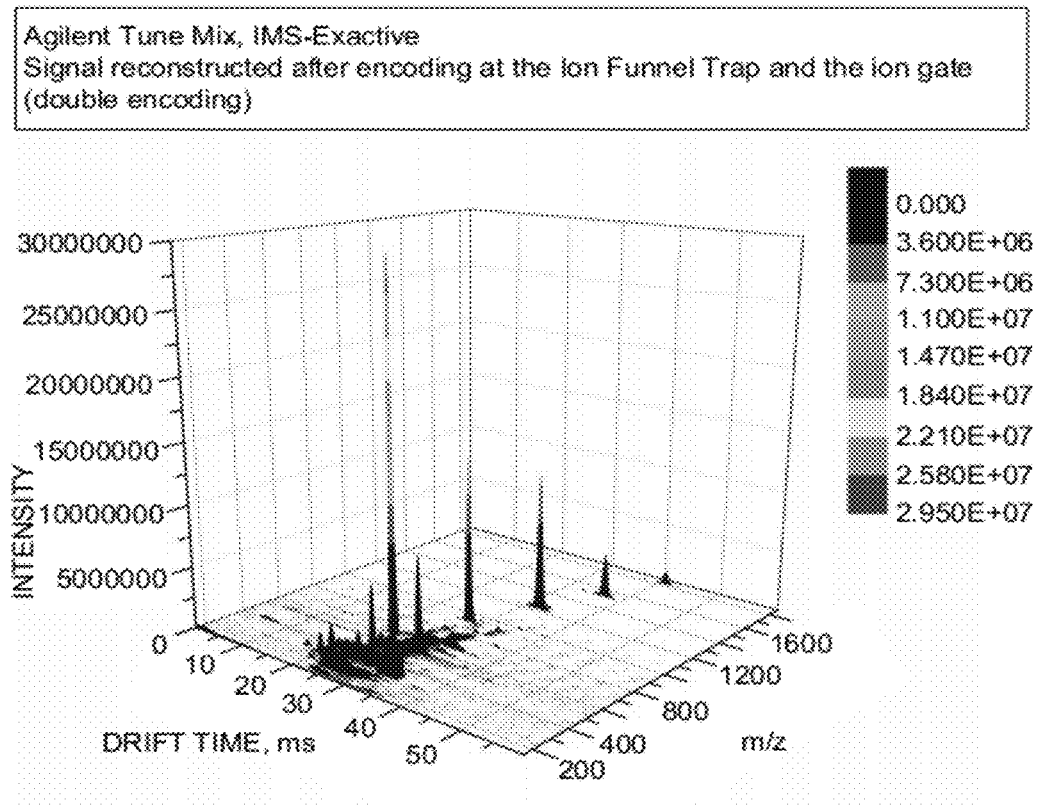
FIG. 12 is a graph showing the complete reconstructed 3D surface plot of the raw data shown in FIG. 9-10 from an experiment demonstrating a preferred embodiment of the apparatus of the present invention.

The characteristic feature of the double multiplexed experiments is that species at a given m/z produce signals at every sub-modulation bin of the encoding sequence. Analysis of the double encoded and reconstructed IMS domains is shown in FIG. 11. These results are depicted for several m/z ranges and demonstrate significant signal enhancements for the decoded data. FIG. 12 shows the complete reconstructed 3D surface plot of the raw data shown in FIG. 9-10. Similar to the 2D plot in FIG. 11, these data indicate drastic reduction in the chemical background levels and enhancements in the signal amplitudes. In addition, the double multiplexed mode results in over an order of magnitude signal intensities as compared to the reconstructed results from the single multiplexed study.

In summary, the developed multiplexed approaches have been demonstrated to be a powerful tool for coupling 'fast' separations and 'slow' detection systems. The combination of IMS-Orbitrap (or Fourier Transform Ion Cyclotron Resonance MS) is one example of how the present invention can provide an attractive and versatile platform for top-down and middle-down proteomics, as well as system biology applications.

While the invention has been illustrated and described in detail in the drawings and foregoing description, the same is to be considered as illustrative and not restrictive in character. Only certain embodiments have been shown and described, and all changes, equivalents, and modifications that come within the spirit of the invention described herein are desired to be protected. Any experiments, experimental examples, or experimental results provided herein are intended to be illustrative of the present invention and should not be considered limiting or restrictive with regard to the invention scope. Further, any theory, mechanism of operation, proof, or finding stated herein is meant to further enhance understanding of the present invention and is not intended to limit the present invention in any way to such theory, mechanism of operation, proof, or finding.

Thus, the specifics of this description and the attached drawings should not be interpreted to limit the scope of this invention to the specifics thereof. Rather, the scope of this invention should be evaluated with reference to the claims appended hereto. In reading the claims it is intended that when words such as "a", "an", "at least one", and "at least a portion" are used there is no intention to limit the claims to only one item unless specifically stated to the contrary in the claims. Further, when the language "at least a portion" and/or "a portion" is used, the claims may include a portion and/or the entire items unless specifically stated to the contrary. Likewise, where the term "input" or "output" is used in connection with an electric device or fluid processing unit, it should be understood to comprehend singular or plural and one or more signal channels or fluid lines as appropriate in the context. Finally, all publications, patents, and patent applications cited in this specification are herein incorporated by reference to the extent not inconsistent with the present disclosure as if each were specifically and individually indicated to be incorporated by reference and set forth in its entirety herein.

The invention claimed is:

1. A system, comprising:
an ion mobility separation stage with a drift region therein coupled to an ion trap mass spectrometer, wherein the separation stage is configured to receive two or more ion packets comprising ions from multiple analytes in a sample in succession from an ion funnel at time intervals that are other than constant encoded by a first pulse sequence that separates the ions in the drift region therein;
an ion gate disposed at an end of the drift region in front of the ion trap mass spectrometer; and
control circuitry configured to release ions in two or more separated ion packets from the drift region through the ion gate into the ion trap mass spectrometer at time intervals encoded by a second pulse sequence within the acquisition time of the ion trap mass spectrometer.

2. The system of claim 1, wherein the second pulse sequence includes a binary term $2^N-1$ that defines the number of ion releases through the ion gate where N is the number of data bits in the second pulse sequence.

3. The system of claim 1, wherein the ion funnel includes an ion funnel trap at the exit end thereof that accumulates ions in the two or more ion packets for delivery into the drift region of the ion mobility separation stage.

4. The system of claim 1, wherein the control circuitry synchronizes the second pulse sequence that releases ions from the mobility separation stage at a selected delay through the ion gate into the ion trap mass spectrometer with the first pulse sequence that introduces ions from the ion funnel into the drift region of the mobility separation stage.

5. A method for analyzing a sample containing multiple analytes, the method comprising the steps of:
introducing two or more ion packets comprising accumulated ions from the multiple analytes in the sample in succession from an ion funnel into a drift region of an ion mobility separation stage at time intervals that are other than constant and encoded by a first pulse sequence;
separating ions in the two or more ion packets in the drift region of the ion mobility separation stage at each of the time intervals to obtain separation profiles therefore; and
releasing ions in the two or more separated ion packets with control circuitry from the drift region of the mobility separation stage through an ion gate into the ion trap mass spectrometer at time intervals encoded by a second pulse sequence, wherein the number of ion releases through the ion gate is defined by a binary term $2^N-1$ in the second pulse sequence where N is the number of data bits in the second pulse sequence.

6. The method of claim 5, wherein the first pulse sequence that introduces ions into the drift region of the mobility separation stage is synchronized with the second pulse sequence that releases ions at a selected delay through the ion gate from the mobility separation stage into the ion trap mass spectrometer.

7. The method of claim 5, wherein the introduction of ions into the drift region of the mobility separation stage is performed at a pressure at or below about 4 Torr.

8. The method of claim 5, wherein the introduction of ions in the two or more ion packets into the ion mobility separation stage occurs on a time scale that matches the time scale for separation of a single ion packet therein.

9. The method of claim 5, wherein the release of ions from the mobility separation stage includes acquiring an m/z spectrum for ions released at each time interval from the mobility separation stage into the ion trap mass spectrometer.

10. The method of claim 5, wherein the release of ions includes modulating the second pulse sequence such that the ions are released from the drift region through the ion gate into the ion trap mass spectrometer at a selected delay relative to the ion packets introduced into the drift region by the first pulse sequence.

11. The method of claim 5, wherein the release of ions includes releasing separated ions from the ion mobility separation stage in a series of temporal windows, each temporal window having a selectable time width shorter than the shortest peak width of an individual analyte ion therein such that the individual analyte falls within at least one temporal window.

12. The method of claim 5, wherein the release of ions through the ion gate into the ion trap mass spectrometer includes encoding a 2D spectrum containing both the mobility separation profiles and the m/z profiles for ions released at every time interval from the mobility separation stage.

13. The method of claim 12, further including decoding the encoded 2D spectrum containing mobility separation profiles and m/z profiles for ions released into the ion trap mass spectrometer to obtain an m/z spectrum for all ions in the sample.

14. The method of claim 13, wherein the m/z spectrum includes m/z values for all ions separated in the mobility separation stage at all time intervals in all temporal windows.

15. The method of claim 5, wherein the release of ions from the drift region through the ion gate into the ion trap mass spectrometer is completed within the acquisition time of the ion trap mass spectrometer.

16. The method of claim 5, wherein the release of ions into the ion trap mass spectrometer is performed with a dual multiplexing modulation.

17. The method of claim 5, wherein the first and second pulse sequences are pseudo random pulse sequences.

18. The method of claim 5, wherein the time intervals are pseudo random time intervals.

19. The method of claim 5, wherein the first and second pulse sequences are 4-bit pulse sequences or greater order pulse sequences.

\* \* \* \* \*